United States Patent [19]
Walele et al.

[11] Patent Number: 5,959,130
[45] Date of Patent: Sep. 28, 1999

[54] CASTOR BASED BENZOATE ESTERS

[75] Inventors: Ismail Walele, Saddle Brook; Samad A. Syed, Paramus, both of N.J.

[73] Assignee: Finetex, Inc., Elmwood Park, N.J.

[21] Appl. No.: 08/883,151

[22] Filed: Jun. 27, 1997

Related U.S. Application Data

[60] Provisional application No. 60/021,056, Jul. 2, 1996.
[51] Int. Cl.$^6$ .......................... C07C 53/00; C07C 59/00
[52] U.S. Cl. ........................ 554/220; 554/223; 554/227
[58] Field of Search ................................. 554/220, 223, 554/227

[56] References Cited

U.S. PATENT DOCUMENTS

| | | |
|---|---|---|
| 1,097,308 | 5/1914 | Ellis . |
| 1,135,351 | 4/1915 | Burchenal . |
| 1,187,999 | 6/1916 | Lowenstein . |
| 1,381,057 | 6/1921 | Boedecker . |
| 1,381,564 | 6/1921 | Klein . |
| 1,553,271 | 9/1925 | Shonle et al. . |
| 1,697,337 | 1/1929 | Adams et al. . |
| 1,886,538 | 11/1932 | Fanto . |
| 1,936,457 | 11/1933 | Larson . |
| 2,014,045 | 9/1935 | Hermann . |
| 2,066,759 | 1/1937 | Bent . |
| 2,164,291 | 6/1939 | Jenness . |
| 2,182,397 | 12/1939 | Eckey . |
| 2,207,257 | 7/1940 | Kapp . |
| 2,305,228 | 12/1942 | Woodhouse et al. . |
| 2,392,100 | 1/1946 | Price et al. . |
| 2,402,584 | 6/1946 | Searle . |
| 2,484,328 | 10/1949 | Agster et al. . |
| 2,678,935 | 5/1954 | Sundberg et al. . |
| 2,895,911 | 7/1959 | VanDyke . |
| 2,942,013 | 6/1960 | Bruson et al. . |
| 3,012,049 | 12/1961 | Bill . |
| 3,057,893 | 10/1962 | Smith, Jr. et al. . |
| 3,116,305 | 12/1963 | Morris et al. . |
| 3,322,772 | 5/1967 | Togashi et al. . |
| 3,459,736 | 8/1969 | Dalibor . |
| 3,663,583 | 5/1972 | Haynes . |
| 3,821,264 | 6/1974 | Henrick . |
| 4,004,041 | 1/1977 | Koslowsky . |
| 4,032,550 | 6/1977 | White et al. . |
| 4,038,295 | 7/1977 | Stern et al. . |
| 4,161,483 | 7/1979 | Cahen . |
| 4,215,048 | 7/1980 | Chen et al. . |
| 4,229,361 | 10/1980 | Cahen . |
| 4,303,639 | 12/1981 | Vanlerberghe et al. . |
| 4,388,473 | 6/1983 | Richeter et al. . |
| 4,421,739 | 12/1983 | Bouillon et al. . |
| 4,510,093 | 4/1985 | Hiilsmann . |
| 4,595,537 | 6/1986 | Ochiai et al. . |
| 4,597,906 | 7/1986 | Uhrig et al. . |
| 4,648,996 | 3/1987 | Aig et al. . |
| 4,661,616 | 4/1987 | Hill . |
| 4,737,413 | 4/1988 | Buchanan . |
| 4,764,505 | 8/1988 | Fujinuma et al. . |
| 4,820,508 | 4/1989 | Wortzman . |
| 4,883,613 | 11/1989 | Aig et al. . |
| 4,933,330 | 6/1990 | Jorgensen et al. . |
| 4,933,417 | 6/1990 | Yamamoto et al. . |
| 4,950,688 | 8/1990 | Bowser et al. . |
| 4,970,235 | 11/1990 | Traitler et al. . |
| 5,011,855 | 4/1991 | Traitler et al. . |
| 5,026,551 | 6/1991 | Yorozu et al. . |
| 5,039,516 | 8/1991 | Goodman et al. . |
| 5,069,915 | 12/1991 | Devitt et al. . |
| 5,093,112 | 3/1992 | Birtwistle et al. . |
| 5,141,741 | 8/1992 | Ishida et al. . |
| 5,182,105 | 1/1993 | Takata et al. . |
| 5,202,357 | 4/1993 | Bowser et al. . |
| 5,227,503 | 7/1993 | Hagan et al. . |

OTHER PUBLICATIONS

Yamamoto et al., Journal of Organic Chemistry, vol. 56, No. 20, pp. 5737–5738, 1991.
Ishii et al., chem. abstr. of DE–2,243,236, 1973.

*Primary Examiner*—Samuel Barts
*Assistant Examiner*—Deborah D Carr
*Attorney, Agent, or Firm*—Weingram & Associates, P.C.

[57] ABSTRACT

Compositions of matter comprising castor-based benzoate esters, including benzoate esters of castor oil, benzoate esters of hydrogenated castor oil, benzoate esters of cetyl ricinoleate, and benzoate esters of octyl hydroxy stearate. The benzoate esters of ricinoleic acid and hydroxy stearic acid are double esters having a fatty acid group at the respective —COOH group and a benzoate group at the —OH group. The benzoate esters are useful as vehicles or carriers, emollients or solubilizers for toiletry, cosmetic, hair and skin care formulations.

5 Claims, No Drawings

CASTOR BASED BENZOATE ESTERS

CROSS-REFERENCE TO RELATED APPLICATION

This application is based on provisional application Ser. No. 60/021,056, filed Jul. 2, 1996 and still pending.

BACKGROUND OF THE INVENTION

1. Field of the Invention

This invention relates generally to improved ester compositions, and more particularly to benzoate esters of castor oil, hydrogenated castor oil, ricinoleic acid, and hydroxy stearic acid useful as diluents, solvents, emollients, solubilizers, liquid carriers, vehicles, and the like for cosmetic and toiletry formulations.

2. Description of the Related Art

Esters and acids are known for a variety of different applications for cosmetic, pharmaceutical and medicinal purposes.

For example, U.S. Pat. No. 1,553,271 to SHONLE describes benzyl esters of higher fatty acids, e.g. 10 or more carbon atoms, such as lauric, capric, palmitic, stearic, oleic and linoleic acids. The compounds may be used as "therapeutic" agents. It is preferred to used mixed fatty acids for a lower cost product. The general structure is R—COO—CH$_2$—C$_6$H$_5$, wherein R is an alkyl group containing 9 or more carbon atoms. The benzyl esters of higher fatty acids are prepared by reacting the anhydrous alkali salt of the fatty acid with benzyl chloride in a suitable solvent. This reference does not teach the benzoate esters of stearates or ricinoleates or the 12-hydroxy compounds thereof.

U.S. Pat. No. 2,182,397 to ECKEY describes a process for forming ether derivatives of polyhydric alcohols, including derivatives that contain esterified fatty acid groups. The reaction calls for reacting a polyhydric alcohol in a quantity of a carboxylic acid which is only sufficient to esterify a portion of the hydroxyl groups of each molecule of the polyhedric alcohol entering into the reaction, thus leaving one or more hydroxyl groups in each molecule unesterified. A small quantity of an esterifying catalyst is added. Polyhdric alcohols listed are, e.g. glycerol and the glycols, e.g. ethyl, propylene, trimethylene, and sorbitol and inannitol. The carboxylic acids listed include aromatic acids, such as benzoic acid. Eckey does not teach the preparation of benzoic acid esters of fatty acids.

U.S. Pat. No. 2,942,013 to BRUSON describes reacting halogenated phenols in the presence of an alkaline catalyst with a salt of 9,10-epoxystearic acid to form a salt of halogenated mono-aryl ether of 9,10-dihydroxystearic acid. The compound is called a 9,10-disubstituted stearic acid wherein one substituent is hydroxyl and the other is a halogenated aryloxy (Col. 1, lns. 46–49). The halogenated phenols may have alkoxy as a nuclear substituent. The reference does not teach the preparation of benzoic acid esters of fatty acids.

U.S. Pat. No. 3,012,049 to BILL describes the use of a hindered phenol as catalysts for carboxylic ester-interchange reactions of fatty acid alkyl esters by using lower C-chain alkyl esters of benzoic acid. The reactions are limited to those in which the starting material and the end product are substantially free of unesterified carboxyl groups. (col. 2, lns. 34–37). The reference does not teach the preparation of double esters of fatty acids or triglycerides.

U.S. Pat. No. 3,116,305 to MORRIS describes reacting 3,5-dialkyl hydroxybenzyl alcohols with carboxylic acid to produce esters (col. 2, ln. 55) which have antioxidant properties, miscibility in organic substrates, and sunscreening characteristics. The acids may be alkenoic acids, aliphatic dicarboxylic acids, fatty acids and aromatic acids having up to two rings. Examples include acetic, butyric, caprylic and undecanoic as well as stearic and ricinoleic acids. The reactions are specifically between substituted aromatic alcohols and aliphatic acids. The —OH of ricinoleic or hydroxy stearic acid is not esterified. The reference does not teach the reaction of benzoic acid on the —OH group of the castor based fatty acids backbone in the form of triglycerides (castor oil) or hydrogenated castor oil (castor wax) or ricinoleic acid fatty alkyl ester or hydroxy stearic acid alkyl ester.

U.S. Pat. No. 3,322,772 to TOGASHI et al. describes a process for production of carboxylic acid esters. Benzoic and stearic acids are listed as possible carboxylic acids and polyhydric alcohols (polyols) such as glycerol and aromatic alcohols such as benzyl alcohol are listed as possible alcohols. The reference does not teach or suggest preparation of double esters.

U.S. Pat. No. 3,459,736 to DALIBOR describes a process for producing ester plasticizers using titanium-peroxide containing catalysts. The preparations are polyesters with polyhydric alcohols or polycarboxylic acids or aromatic dicarboxylic acids/anhydrides. Among the alcohols which may be reacted with the carboxylic acids are ricinoleic acid, ricinoleic mono-, di-, triglyceride and ricinoleic methyl ester (col. 4, lns. 45–50). The reference does not teach or suggest preparation of monomeric esters that are double esters of the castor triglycerides or of the —OH containing castor based fatty acids.

U.S. Pat. No. 4,597,906 to UHRIG et al. describes preparations of esters of aromatic alcohols specifically beta-naphthols with fatty acids, transesterified with glycerol and further ethoxylated. The preparation of castor oil-beta-naphthol, its oxyethylation product and its sulfosuccinic acid semiesters is described. The —COOH group of the fatty acids is reacted with either aromatic alcohol such as beta-naphthol or polyhydric alcohol for further ethoxylation. The reference does not teach or suggest preparing double esters using the —OH group of fatty acids for reaction with aromatic acid, not aromatic alcohol, and the —COOH group with mono alcohol and not polyhydric alcohol.

U.S. Pat. No. 5,227,503 to HAGAN describes cosmetic compositions containing unsaturated 2-hydroxyalkenoic acids as skin, hair and nail treatment compositions.

However, among the foregoing patents, none are directed to compositions of benzoic acid esters of glycerol tri-ricinoleate, benzoic acid esters of glycerol trihydroxy stearate (GTHS), benzoate esters of alkyl ricinoleates or benzoic esters of alkyl hydroxy stearates of the present invention, or the advantages which result from these compositions.

OBJECTS AND SUMMARY OF THE INVENTION

It is an object of this invention to provide novel benzoate ester compositions having unique properties which make them uniquely suitable as a vehicle or carrier in toiletry and cosmetic compositions.

It is a further object of this invention to provide benzoate esters having unexpected properties, not taught or suggested by the prior art, which make the compositions uniquely suitable for broad application in toiletry and cosmetic compositions.

Yet another object of this invention is to provide novel castor-based benzoate esters which have improved tactile properties, better spreadability, less tackiness (stickiness) and greasiness on the skin, better suspension properties (TiO$_2$) more effective in wetting and dispersing pigments, which has similar odor and taste, is an excellent D&C red No. 21 solubilizer and is a lighter feeling oil.

The foregoing objects and other objects are obtained by reacting benzoic acid and castor-based raw materials, specifically, the hydroxyl group of castor oil, hydrogenated castor oil, ricinoleic acid or 12-hydroxy stearic acid, a fatty ester of ricinoleic acid or a fatty ester of hydroxy stearic acid. The compositions provided include many unique effects as compared to the raw materials which comprise the compositions.

DETAILED DESCRIPTION OF THE INVENTION

The preparations of novel benozate esters of this invention are referred to herein as castor-based benzoate esters as the basic backbone of the preparations is either naturally occurring castor oil (CO), its hydrogenated analog (HCO), ricinoleic acid (RA) or 12-hydroxy stearic acid (HSA).

The novel benzoate esters of this invention are produced by the reaction of benzoic acid on the hydroxyl group of the castor-based fatty acids backbone in the form of castor oil (triglyceride), hydrogenated castor oil (castor wax), ricinoleic acid fatty alkyl ester or hydroxy stearic acid alkyl ester.

The castor-based fatty acids used in preparing the castor-based benzoate esters, as previously stated, are selected from the group consisting of:

(A) Castor oil (glycerol tri-ricinoleate), hereinafter referred to as "CO", having the following structure:

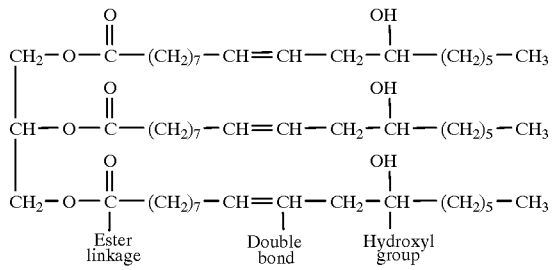

Any technical grade of glyceryl tri-ricinoleate or a triglyceride of hydroxy-bearing unsaturated acid of C8–C18 chain length, preferably of C-18 chain length, with one unsaturation as in oleic acid but with a 12-hydroxy group, may be used.

(B) Hydrogenated castor oil (glyceryl trihydroxy stearate or GTHS), also known as Castor Wax), which is a hydrogenated, i.e., saturated, form of castor oil. It is referred to herein as "HCO", and has the following structure:

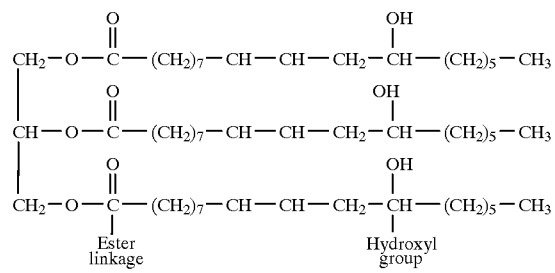

(C) Ricinoleic Acid (12-hydroxy oleic acid), esterified with 2-ethyl hexanol or cetyl alcohol and further esterified with benzoic acid. Ricinoleic acid is referred to herein as "RA" and has the following structure:

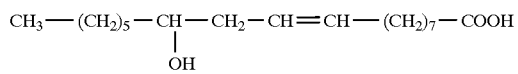

RA is oleic acid having a pendant hydroxy (—OH) group that is available for esterification with benzoic acid in addition to an acid group that is also available for esterification with fatty alcohol.

(D) Hydroxy Stearic Acid hereinafter referred to as "HSA", is a hydrogenated, solid form of ricinoleic acid having the following structure:

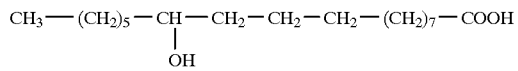

HSA, otherwise referred to as 12-hydroxy stearic acid, is saturated C-18 acid (stearic acid) containing a hydroxy group at the 12-carbon position which is available for reaction with benzoic acid and having a —COOH group which is available for esterification with fatty alcohols.

The esters of ricinoleic acid (RA) and hydroxy stearic acid (HSA) are double esters. A fatty ester moiety is on the —COOH group of RA or HSA, respectively, and the benzoyl (-C6H5CO) ester moiety, i.e., the benzoate group, is on the —OH group.

The fatty alcohols for reaction with the —COOH group may be C8–C18 alcohols of single Cx (where x=8, . . . 18) chains or the mixtures of any combinations of C8–C18 alcohols. The preferred fatty alcohols are selected from the group consisting of cetyl alcohol (C16 or hexadecyl alcohol), octyl alcohol (linear C8 alcohol) and 2-ethyl hexanol.

The structure of 2-ethyl hexanol is:

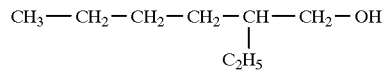

The structure of cetyl alcohol (hexadecyl alcohol) is:

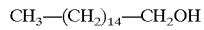

As castor oil is a triglyceride of Hydroxy-Ricinoleic Acid, the available hydroxyl group of the ricinoleic chain reacts with benzoic acid to produce the benzoic acid ester of glyceryl tri-ricinoleate, i.e., the benzoic acid ester of castor oil.

As hydrogenated castor oil is a triglyceride of Hydroxy Stearic Acid, the available hydroxyl group of the Hydroxy Stearic chain reacts with benzoic acid to produce the benzoic acid ester of glyceryl-trihydroxy stearate, i.e., benzoic acid ester of hydrogenated castor oil.

Ricinoleic acid is a castor-based hydroxy-oleic acid. The carboxylic group is esterified with a fatty alcohol such as Cetyl Alcohol or 2 Ethyl-Hexanol, and then further esterified at the hydroxyl group with benzoic acid to produce benzoate esters of alkyl-ricinoleate. An example of the preparation is benzoic acid ester of cetyl-ricinoleate.

Hydroxy Stearic Acid is a castor-based hydrogenated ricinoleic acid, also called 12-hydroxy stearic Acid. The carboxylic group and the hydroxyl group are respectively used for reaction as in the case of ricinoleic acid to prepare behzoate esters of Alkyl-Hydroxy-Stearate. An example of the preparation is the benzoic acid ester of 2 ethyl hexyl 12-hydroxy stearate.

Benzoic acid ester of glyceryl tri-ricinoleate, i.e benzoic acid ester of castor oil has the following structure:

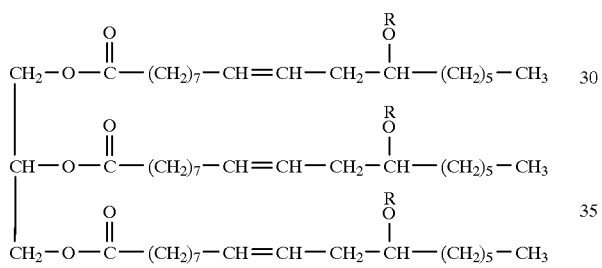

wherein R is:

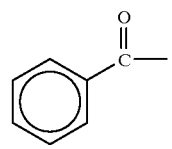

Benzoic acid ester of glyceryl-trihydroxy stearate, i.e. benzoic acid ester of hydrogenated castor oil has the following structure:

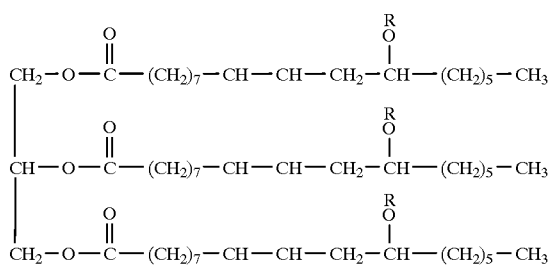

wherein R is:

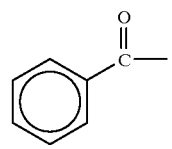

Benzoate ester of alkyl ricinoleate has the structure:

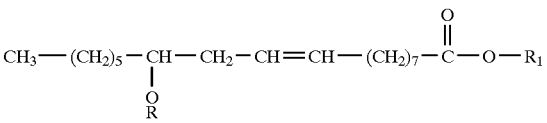

wherein $R_1$ is branched or linear alkyls of 8 to 16 carbon atoms, for example, 2-ethyl-hexyl or hexadecyl substituents wherein R is:

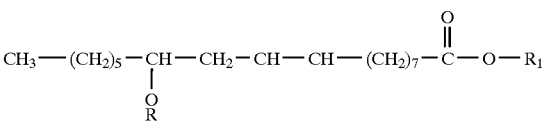

Benzoate ester of alkyl hydroxy stearate has the structure:

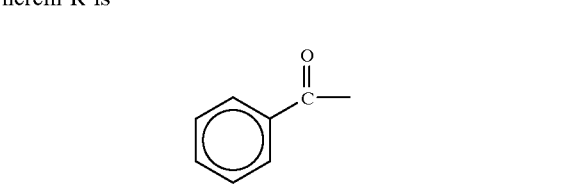

wherein $R_1$ is branched or linear alkyls of 8 to 16 carbon atoms, for example, 2-ethyl-hexyl or hexadecyl substituants, wherein R is

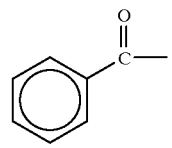

Thus, the esters of the invention are of three types:
a. fatty acid triglycerides as (naturally occurring) castor oil, the —OH of the fatty chain further esterified with benzoic acid;
b. fatty acid esters further esterified on the —OH group (of the starting OH-containing fatty acids) with benzoic acid; and
c. triglycerides of hydroxystearic acid further esterified with benzoic acid.

The compositions of this invention are produced by reacting benzoic acid with the castor-based fatty acids. Preferably, stannous oxalate is used as a catalyst. It is contemplated, however, that any method of producing such benzoate esters may be utilized insofar as such method does not interfere with the intended use of the compositions, particularly in the cosmetic and toiletry field. The process for producing the benzoate esters of this invention should permit them to be purified to a substantially pure condition, by which is meant that the compositions do not contain impurities which interfere with their intended use, particularly as carriers or vehicles in toiletry and cosmetic formulations.

The aforedescribed benzoate esters have unique properties that make them particularly suited for use as emollient carriers for cosmetic ingredients. The aforedescribed benzoate esters have improved tactile properties, better spreadability, less tackiness and greasiness on the skin, lighter feeling oil (despite oil at approximately 937 cps. vs. 770 cps. of castor oil), better suspension properties ($TiO_2$), excellent D&C Red No. 21 solubilizer, more effective in wetting and dispersing pigments, similar odor and taste. Castor-oil benzoate is miscible with liquid octyl-methoxycinnamate, and with benzophenone-3 and Parsol® 1789 in specific ratios as shown in Tables IVA and IVB below. Parsol® is a registered trademark of Givaudan Corp. of Clifon, N.J.

The benzoate esters of the invention are useful in skin care compositions, e.g., compositions applied to the skin which soften or soothe the skin and which cosmetically affect the skin, such as by cleansing, reducing or enhancing odor, sun-blocking, etc. The skin care compositions in which the esters of the invention may be used include, but are not limited to, hand cleansers, bath oils, suntan oils, sun blocks, anti-perspirants, deodorants, perfumes, colognes, cold creams, electric pre-shaves, topical pharmaceutical ointments, lipsticks, rouges, lotions, skin moisturizers, cleansing creams or after-bath splashes or lotions.

The amount used in skin care compositions depends on the type of skin care composition, the type and quantity of cosmetic ingredients used and the amount and type of functional additives. Typically, the amount ranges from about 1% to about 20%, by weight, of the skin care compositions. For example, a facial cream may only have about 1% to 4% by weight, whereas skin lotions may have up to about 5% to 8% by weight. Still higher amounts may be used in, for example, sunscreens, at 15% to 20% by weight.

DESCRIPTION OF THE PREFERRED EMBODIMENTS

The following, non-limiting Examples 1 through 15 set forth typical procedures and results yielded in the course of preparing the castor-based benzoate ester compositions of the invention.

Examples 1–5 below illustrate the preparation of benzoate esters based on castor oil (glyceryl tri-ricinoleate). Examples 6 and 7 demonstrate the preparation of benzoate esters based on hydrogenated castor oil (glyceryl trihydroxy stearate). Examples 8 through 11 concern the preparation of benozate esters of cetyl ricinoleate (identified as "CR" or cetyl ester of ricinoleic acid) and examples 12 through 15 relate to the preparation of benozate esters of octyl hydroxy stearate (2-ethyl hydroxy stearate).

EXAMPLE #1
Preparation of Castor Oil Benzoate (77- 155)

In 500 ml. four neck round bottom flask equipped with glass stirrer, distillation head, condenser and receiver added 209 grams (1.0 moles) of castor oil #1 and 41.00 grams (1.50 moles) of benzoic acid. The temperature was raised to 60° C. under nitrogen. At 60° C., added 0.375 grams of stannous oxalate and continued to heat to 200° C. maintaining a good flow of nitrogen over 60 minutes. The reaction mixture was then raised to 220° C. in next 30 minutes and held for 2 hours. The distillate collected was 6.0 grams against theoretical estimates of 6.05 grams. The ester had the acidity of 2.61 mg KOH/g. The reaction product was treated with 235 grams of deionized water containing 1 gram of sodium carbonate, 22 grams of sodium sulfate at 80° C. The ester was allowed to stand overnight. The top layer containing the benzoate ester was collected. It was vacuum stripped at 115°–120° C. and 10–15 mm of Hg vacuum. 40 grams of isopropanol was added to thin out the product. The liquid benzoate of this reaction was then treated with 0.2 grams each of magnesol (synthetic magnesium silicate) and celaton FW 60 (diatomaceous earths) at 50° C. The product was filtered through Buckner Funnel with Whatman Paper #4 at 50° C. The product containing isopropanol was again heated to 80° C. to distill off isopropanol. The net yield of the benzoate ester product was 195.6 grams.

EXAMPLE #2
Preparation of Castor Oil Benzoate (86-09)

In 1000 ml. four neck round bottom flask equipped with glass stirrer, distillation head, condenser and receiver added 313.5 a grams (1.0 moles) of castor oil #1 and 61.5 grams (1.5 moles) of benzoic acid. The temperature was raised to 60° C. with a good flow of nitrogen. At 60° C., added 0.60 grams of stannous oxalate and continued to heat to 200° C. maintaining a good flow of nitrogen over 60 minutes. The reaction mixture was then raised to 220° C. in next 30 minutes and held for three hours. The distillate collected was 9.0 grams against theoretical estimates of 9.10 grams. The ester had the acidity of 4.10 mg KOH/g. The reaction product was treated with 300 grams of deionized water containing 5 grams of sodium carbonate and 33 grams of sodium sulfate at 80° C. The top layer containing the benzoate ester was collected. It was vacuum stripped at 115° C.–120° C. and 10–15 mm of Hg vacuum. The liquid benzoate of this reaction was then treated with 0.1 gram each of magnesol (synthetic magnesium silicate), celaton at 60 (diatomaceous earths) at 75° C. The product was filtered through a filter press with Whatman Paper #4 at 75° C. The net yield of the benzoate ester product was 300 grams.

EXAMPLE #3
Preparation of Castor Oil Benzoate (87-158)

In 2000 ml. four neck round bottom flask equipped with glass stirrer, distillation head, condenser and receiver added 836.00 grams (1.0 moles) of castor oil #1 and 164 grams (1.5 moles) of benzoic acid. The temperature was raised to 60° C. with a good flow of nitrogen. At 60° C., added 1.5 grams of stannous oxalate and continued to heat to 200° C. maintaining a good flow of nitrogen over 60 minutes. The reaction mixture was then raised to 240° C. in next 60 minutes and held for 2 hours. The distillate collected was 24 is grams against theoretical estimates of 24.20 grams. The ester had the acidity of 4.96 mg KOH/g. The reaction product was treated with 10 grams of 35% hydrogen peroxide at 100° C. for one hour. The reaction product was treated with 900 grams of deionized water containing 7.5 grams of sodium carbonate and 85 grams of sodium sulfate at 80° C. The top layer containing the benzoate ester was collected. It was vacuum stripped at 115°–120° C. and 10–15 mm of Hg vacuum. The liquid benzoate of this reaction was then treated with 0.2 grams each of magnesol, celaton FW 60 (diatomaceous earths) at 75° C. The product was filtered through a filter press with Whatman Paper #4 at 75° C. The net yield of the benzoate ester product was 800 grams.

EXAMPLE #4
Preparation of Castor Oil Benzoate (87-114)

In 3000 ml. four neck round bottom flask equipped with glass stirrer, distillation head, condenser and receiver added 1254 grams (1.0 moles) of castor oil #1 and 246 grams (1.5 moles) of benzoic acid. The temperature was raised to 60° C. with a good flow of nitrogen. At 60° C., added 2.25 grams of stannous oxalate and continued to heat to 200° C. maintaining a good flow of nitrogen over 60 minutes. Held at this temperature (200° C.) for 2 hours. The reaction mixture was then raised to 240° C. in next 60 minutes and held for 2 hours. The distillate collected was 36.0 grams against theoretical estimates of 36.30 grams. The ester had the acidity of 2.5 mg KOH/g. The reaction product was treated with 30 grams of 35% hydrogen peroxide at 100° C. for one hour. The reaction product was treated with 1200 grams of deionized water containing 5 grams of sodium carbonate and 132 grams of sodium sulfate at 80° C. The top layer containing the benzoate ester was collected. It was vacuum stripped at 115°–120° C. and 10–15 mm of Hg vacuum. The liquid benzoate of this reaction was then treated with 0.2 grams each of magnesol, celaton FW 60 (diatomaceous earths) at 75° C. The product was filtered through filter press with Whatman Paper #4 at 75° C. The net yield of the benzoate ester product was 1300 grams.

EXAMPLE #5
Preparation of Castor Oil Benzoate (107-34)

In 3000 ml. four neck round bottom flask equipped with glass stirrer, distillation head, condenser and receiver added 1254 grams (1.0 moles) of castor oil #1 and 246 grams (1.5 moles) of benzoic acid. The temperature was raised to 60° C. with a good flow of nitrogen. At 60° C., added 7.5 grams of stannous oxalate and continued to heat to 240° C. maintaining a good flow of nitrogen over 2 hours and held for 2 hours. The distillate collected was 36.20 grams against theoretical estimates of 36.30 grams. The ester had the acidity of 1.2 mg KOH/g. The reaction product cooled to 40° C. and filtered on filter press with Whatman Paper #4. The net yield 40 of the benzoate ester product was 1460 grams.

EXAMPLE #6
Preparation of Castor Wax MP-80 Benzoate (75-154)

In 500 ml. four neck round bottom flask equipped with glass stirrer, distillation head, condenser and receiver added 190 grams (1.0 moles) of castor wax MP-80 (hydrogenated castor oil) and 37.19 grams (1.5 moles) of benzoic acid. The temperature was raised to 80° C. with a good flow of nitrogen. At 80° C., added 0.34 grams of stannous oxalate and continued to heat to 200° C. maintaining a good flow of nitrogen over 60 minutes. The reaction mixture was then raised to 220° C. in next 60 minutes and held for 2 hours. The distillate collected was 5.0 grams against theoretical estimates of 5.48 grams. The ester had the acidity of 5.6 mg KOH/g. The reaction product was treated with 175 grams of deionized water containing 2 grams of sodium carbonate and 14 grams of sodium sulfate at 80° C. The top layer containing the benzoate ester was collected. It was vacuum stripped at 115°–120° C. and 10–15 min of Hg vacuum. The benzoate of this reaction was then treated with 0.05 grams each of magnesol, celaton FW 60 (diatomaceous earths) at 75° C. The product was filtered through a filter press with Whatman Paper #4 at 75° C. The net yield of the benzoate ester product was 180 grams.

EXAMPLE #7
Preparation of Castor Wax MP-80 Benzoate (77-58)

In 500 ml. four neck round bottom flask equipped with glass stirrer, distillation head, condenser and receiver added 179.4 grams (1.0 moles) of castor wax MP-80 and 70.2 grams (3.0 moles) of benzoic acid. The temperature was raised to 80° C. with a good flow of nitrogen. At 80° C., added 0.40 grams of stannous oxalate and continued to heat to 200° C. maintaining a good flow of nitrogen over 60 minutes. The reaction mixture was then raised to 220° C. in next 60 minutes and held for 4 hours. The distillate collected was 9.35 grams against theoretical estimates of 10.35 grams. The ester had the acidity of 17.17 mg KOH/g. The reaction product was treated with 100 grams of deionized water containing 3.5 grams of sodium carbonate and 30 grams of sodium sulfate at 80° C. The top layer containing the benzoate ester was collected. It was vacuum stripped at 115°–120° C. and 10–15 mm of Hg vacuum. 50 grams of isopropanol was added to thin out product. The liquid benzoate of this reaction was then treated with 0.2 grams each of magnesol, celaton FW 60 (diatomaceous earths) at 50° C. The product was filtered through Buckner Funnel with Whatman Paper #4 at 50° C. The product containing isopropanol was again heated to 80° C. to strip isopropanol. The net yield of the benzoate ester product was 115 grams.

EXAMPLE #8
Preparation of Benzoate Ester of Cetyl Ricinoleate (77-100)

In 500 ml. four neck round bottom flask equipped with glass stirrer, distillation head, condenser and receiver added 200 grams (1.0 moles) of cetyl ricinoleate and 50 grams (1.1 moles) of benzoic acid. The temperature was raised to 60° C. with a good flow of nitrogen. At 60° C., added 0.50 grams of stannous oxalate and continued to heat to 200° C. maintaining a good flow of nitrogen over 60 minutes. The reaction mixture was then raised to 220° C. in next 30 minutes and held for 2 hours. The distillate collected was 6.75 grams against theoretical estimates of 6.75 grams. The ester had the acidity of 8.35 mg KOH/g. The reaction product was treated with 120 grams of deionized water containing 2.36 grams of sodium carbonate and 15 grams of sodium sulfate at 80° C. The top layer containing the benzoate ester was collected. It was vacuum stripped at 115°–120° C. and 10–15 mm of Hg vacuum. 50 grams of isopropanol was added to thin out product. The liquid benzoate of this reaction was then treated with 0.2 grams each of magnesol, celaton FW 60 (diatomaceous earths) at 50° C. The product was filtered through a filter press with Whatman Paper #4. The net yield of the benzoate ester product was 200 grams.

EXAMPLE #9
Preparation of Benzoate Ester of Cetyl Ricinoleate (103-123)

In 2000 ml. four neck round bottom flask equipped with glass stirrer, distillation head, condenser and receiver added 426.7 grams (1.0 moles) of ricinoleic acid and 381.2 grams (1.10 moles) of cetyl alcohol. The temperature was raised to 60° C. with a good flow of nitrogen. At 60° C., added 2.42 grams of stannous oxalate and continued to heat to 200° C. maintaining a good flow of nitrogen over 60 minutes. The reaction mixture was then raised to 220° C. in next 60 minutes and held for 2 hours. The distillate collected was 25 grams against theoretical estimates of 25.77 grams. The ester had the acidity of 1.8 mg KOH/g. The reaction product (cetyl ricinoleate) was cooled to 100° C. and added 192.1 grams (1.10 moles) of benzoic acid. The temperature was raised to 230° C. in next 2 hours and held the reaction product at 230° C. for 3 hours. The distillate collected was 25.0 grams against theoretical estimates of 25.76 grams. The ester had the acidity of 9.10 mg KOH/g. The reaction product was treated with 700 grams of deionized water containing 6.87 grams of sodium carbonate and 140 grams of sodium sulfate at 80° C. The top layer containing the benzoate ester was collected. It was vacuum stripped at 115°–120° C. and 10–15 mm of Hg vacuum. The liquid benzoate of this reaction was then treated with 0.2 grams each of magnesol, celaton FW 60 (diatomaceous earths) at 50° C. 200 grams of isopropanol was added to thin out the product. The product was filtered through a filter press with Whatman Paper #4. The product containing isopropanol was again heated to 80° C. to strip isopropanol. The net yield of the benzoate ester product was 700 grams.

EXAMPLE #10
Preparation of Benzoate Ester of Cetyl Ricinoleate (107-26)

In 3000 ml. four neck round bottom flask equipped with glass stirrer, distillation head, condenser and receiver added 934.8 grams (1.0 moles) of ricinoleic acid and 759.0 grams (1.0 moles) of cetyl alcohol. The temperature was raised to 60° C. with a good flow of nitrogen. At 60° C., added 6.0 grams of stannous oxalate and continued to heat to 200° C. maintaining a good flow of nitrogen over 60 minutes. The reaction mixture was then raised to 220° C. in next 60 minutes and held for 2 hours. The distillate collected was 56.0 grams against theoretical estimates of 56.46 grams. The ester had the acidity of 0.8 mg KOH/g. The reaction product (cetyl ricinoleate) was cooled to 100° C. and added 306.2 grams (0.8 moles) of benzoic acid. The temperature of the reaction mixture was raised to 240° C. over the next 2 hours and held the reaction mass at 240° C. for 3 hours. The distillate collected was 45 grams against theoretical estimates of 45.17 grams. The ester had the acidity of 1.2 mg KOH/g. The reaction mixture was cooled to 100° C. and added 2.0 grams of 35% hydrogen peroxide. The resulting improved color ester was cooled to 40°. The liquid benzoate of this reaction was then treated with 0.7 grams each of magnesol, celaton FW 60 (diatomaceous earths) at 40° C. The product was filtered through a filter press with Whatman Paper #4. The net yield of the benzoate ester product was 1900 grams.

EXAMPLE #11
Preparation of Benzoate Ester of Cetyl Ricinoleate (107-30)

In 3000 ml. four neck round bottom flask equipped with class stirrer, distillation head, condenser and receiver added 934.8 grams (1.0 moles) of ricinoleic acid and 759.0 grams (1.0 moles) of cetyl alcohol. The temperature was raised to 60° C. with a good flow of nitrogen. At 60° C., added 6.0 grams of stannous oxalate and continued to heat to 200° C. maintaining a good flow of nitrogen over 60 minutes. The reaction mixture was then raised to 220° C. in next 60 minutes and held for 2 hours. The distillate collected was 56.0 grams against theoretical estimates of 56.46 grams. The ester had the acidity of 0.8 mg KOH/g. The reaction product (cetyl ricinoleate) was cooled to 100° C. and added 306.2 grams (0.8 moles) of benzoic acid. The temperature of the reaction mixture was raised to 240° C. in next 2 hours and held the reaction mass at 240° C. for 3 hours. The distillate collected was 45 grams against theoretical estimates of 45.17 grams. The ester had the acidity of 1.2 mg KOH/g. The liquid benzoate of this reaction was cooled to 40° C. The product was filtered through a filter press with Whatman Paper #4. The net yield of the benzoate ester product was 1900 grams.

EXAMPLE #12
Preparation of Benzoate Ester of Octylhydroxy Stearate (105-185)

In 500 ml. four neck round bottom flask equipped with glass stirrer, distillation head, condenser and receiver added 248.49 grams (1.0 moles) of octyl hydroxy stearate and 51.51 grams (0.7 moles) of benzoic acid. The temperature was raised to 60° C. with a good flow of nitrogen. At 60° C., added 1.50 grams of stannous oxalate and continued to heat to 200° C. maintaining a good flow of nitrogen over 60 minutes. The reaction mixture was then raised to 220° C. in next 90 minutes and held for 3½ hours. The distillate collected was 7.2 grams against theoretical estimates of 7.60 grams. The ester had the acidity of 0.8 mg KOH/g. The reaction mixture was cooled to 40° C. The liquid benzoate ester of this reaction was then treated with 0.3 grams each of magnesol, celaton FW 60 (diatomaceous earths) at 40° C. The product was filtered through a filter press with Whatman Paper #4. The net yield of the benzoate ester product was 290 grams.

EXAMPLE #13
Preparation of Benzoate Ester of Octylhydroxy Stearate (86-124)

In 2000 ml. four neck round bottom flask equipped with glass stirrer, distillation head, condenser and receiver added 526.0 grams (1.0 moles) of 12-octyl hydroxy stearic acid and 242.6 grams (1.10 moles) of 2-ethyl hexanol. The temperature was raised to 80° C. with a good flow of nitrogen. At 80° C., added 2 grams of stannous oxalate and continued to heat to 200° C. maintaining a good flow of nitrogen over 60 minutes. The reaction mixture was then raised to 220° C. in next 90 minutes and held for 2 hours. The distillate collected was 30.0 grams. The ester had the acidity of 0.60 mg KOH/g. The reaction mixture was cooled to 100° C. and added 227.64 grams (1.10 moles) of benzoic acid. The temperature was raised to 220° C. in next 2 hours and held for 3 hours. The distillate collected was 26 grams against theoretical estimates of 30 grams. The ester had the acidity of 20 mg KOH/g. The reaction product was treated with 800 grams of deionized water containing 18.8 grams of sodium carbonate and 80 grams of sodium sulfate at 80° C.

and kept overnight for good separation. The top layer containing the benzoate ester was collected. It was vacuum stripped at 115°–120° C. and 10–15 mm of Hg vacuum. The liquid benzoate ester of this reaction was then treated with 0.2 grams each of magnesol, celaton FW 60 (diatomaceous earths) at 50° C. 200 grams of isopropanol was added to thin out the product. The product was filtered through a filter press with Whatman Paper #4. The product containing isopropanol was again heated to 80° C. to strip isopropanol. The net yield of the benzoate ester product was 720 grams.

EXAMPLE #14
Preparation of Benzoate Ester of Octylhydroxy Stearate (105-183)

In 1000 ml. four neck round bottom flask equipped with glass stirrer, distillation head, condenser and receiver added 347.1 grams (1.0 moles) of 12-hydroxy stearic acid and 154.2 grams (1.025 moles) of 2-ethyl hexanol. The temperature was raised to 80° C. with a good flow of nitrogen. At 80° C., added 1.0 grams of stannous oxalate and continued to heat to 200° C. maintaining a good flow of nitrogen over 60 minutes. The reaction mixture was then raised to 230° C. in next 90 minutes and held for 1 hour. The distillate collected was 19.82 grams against theoretical estimates of 20.82 grams. The ester (octylhydroxy stearate) had the acidity of 0.1 mg KOH/g. The reaction mixture was cooled to 100° C. and added 98.7 grams (0.70 moles) of benzoic acid and 3.0 grams of stannous oxalate. The temperature was raised to 220° C. in next 2 hours and held for 3 hours. The distillate collected was 14.00 grams against theoretical estimates of 14.32 grams. The ester had the acidity of 0.7 mg KOH/g. The reaction mixture was cooled to 100° C. and added 1 gram of 35% hydrogen peroxide. The resulting improved color ester was cooled to 40° C. The liquid benzoate of this reaction was then treated with 0.2 grams each of magnesol, celaton FW 60 (diatomaceous earths) at 40° C. The product was filtered through a filter press with Whatman Paper #4. The net yield of the benzoate ester product was 250 grams.

EXAMPLE #15
Preparation of Benzoate Ester of Octylhydroxy Stearate (107-33)

In 3000 ml. four neck round bottom flask equipped with glass stirrer, distillation head, condenser and receiver added 879.60 grams (1.0 moles) of 12-hydroxy stearic acid and 378.00 grams (1.025 moles) of 2-ethyl hexanol. The temperature was raised to 80° C. with a good flow of nitrogen. At 80° C., added 4.5 grams of stannous oxalate and continued to heat to 200° C. maintaining a good flow of nitrogen. The reaction mixture was then raised to 230° C. in next 90 minutes and held for 1 hour. The distillate collected was 50.70 grams against theoretical estimates of 51.10 grams. The ester had the acidity of 0.1 mg KOH/g. The reaction mixture (octylhydroxy stearate) was cooled to 100° C. and added 242.40 grams (0.70 moles) of benzoic acid. The temperature was raised to 240° C. in next 3 hours and held for 2 hours. The distillate collected was 35.00 grams against theoretical estimates of 35.76 grams. The ester had the acidity of 0.7 mg KOH/g. The liquid benzoate ester of this reaction was cooled to 40° C. The product was filtered through a filter press with Whatman Paper #4. The net yield of the benzoate ester product was 1404 grams.

The Table of Identification set forth below identifies the benzoate esters of the invention. For ease of identification, each ester is identified by an example number, a three or four letter code, and a reference number. This identification system is used in the subsequent Tables I through VII.

TABLE OF IDENTIFICATION

| EXAMPLE NO. | CODE | REF. NO. |
|---|---|---|
| 1 | BCO[1] | 77-155 |
| 2 | BCO | 86-09 |
| 3 | BCO | 87-158 |
| 4 | BCO | 87-114 |
| 5 | BCO | 107-34 |
| 6 | BHCO[2] | 75-154 |
| 7 | BHCO | 77-58 |
| 8 | BCR3 | 77-100 |
| 9 | BCR | 103-123 |
| 10 | BCR | 107-26 |
| 11 | BCR | 107-30 |
| 12 | BOHS[4] | 105-185 |
| 13 | BOHS | 86-124 |
| 14 | BOHS | 105-183 |
| 15 | BOHS | 107-33 |

[1]BCO = benzoate esters of castor oil
[2]BHCO = benzoate esters of hydrogenated castor oil
[3]BCR = benzoate esters of cetyl ricinoleate
[4]BOHS = benzoate esters of octyl hydroxy stearate

PROPERTIES OF AND USES FOR BENZOATE ESTERS COMPOSITIONS

An analysis of the benzoate esters of Examples 1 through 15 was conducted as to appearance, color, percentage water, acidity (mg KOH/g), saponification (mg KOH/g), and refractive index. The results are presented in Table I.

TABLE I

ANALYTICAL RESULTS OF NOVEL BENZOATE ESTERS

| Ex. No. | Code | Ref. No. | Appearance | Color * | Water % | Acidity | Saponification mg KOH/g | Refract. Index mg KOH/g |
|---|---|---|---|---|---|---|---|---|
| 1. | BCO | 77-15 | Liquid | 3 | 0.05 | 0.46 | 197.40 | 1.4870 |
| 2. | BCO | 86-09 | Liquid | 3 | 0.07 | 0.87 | 215.50 | 1.4870 |
| 3. | BCO | 87-158 | Liquid | 3 | 0.04 | 0.35 | 220.70 | 1.4900 |
| 4. | BCO | 87-114 | Liquid | 3 | 0.02 | 0.50 | 210.40 | 1.4890 |
| 5. | BCO | 107-34 | Liquid | 3 | 0.01 | 0.80 | 230.81 | 1.4915 |
| 6. | BHCO | 75-154 | Liquid | 3 | 0.08 | 0.70 | 224.55 | 1.4780 |
| 7. | BHCO | 77-58 | Liquid | 3 | 0.10 | 0.80 | 260.10 | 1.4870 |

TABLE I-continued

ANALYTICAL RESULTS OF NOVEL BENZOATE ESTERS

| Ex. No. | Code | Ref. No. | Appearance | Color * | Water % | Acidity | Saponification mg KOH/g | Refract. Index mg KOH/g |
|---|---|---|---|---|---|---|---|---|
| 8.  | BCR  | 77-100  | Liquid | 4 | 0.10 | 0.70 | 170.50 | 1.4780 |
| 9.  | BCR  | 103-123 | Liquid | 4 | 0.10 | 1.50 | 155.70 | 1.4765 |
| 10. | BCR  | 107-26  | Liquid | 4 | 0.08 | 1.20 | 158.50 | 1.4770 |
| 11. | BCR  | 107-30  | Liquid | 4 | 0.02 | 1.20 | 160.50 | 1.4775 |
| 12. | BOHS | 105-185 | Liquid | 3 | 0.08 | 0.70 | 195.10 | 1.4750 |
| 13. | BOHS | 86-124  | Liquid | 3 | 0.05 | 0.50 | 210.50 | 1.4760 |
| 14. | BOHS | 105-183 | Liquid | 3 | 0.10 | 0.70 | 190.10 | 1.4740 |
| 16. | BOHS | 107-33  | Liquid | 3 | 0.07 | 0.78 | 195.20 | 1.4750 |

*Color is measured on the Gardnor scale.

Physical Properties

Table II compares the physical properties of the three groups of novel benzoate esters of the invention to the properties of their respective precursor single esters/triglycerides, as follows:

A. Benzoate esters of castor oil (code BCO) are compared to the corresponding precursor, castor oil (Code CO);

B. Benzoate esters of Cetyl Ricinoleate (Code BCR) are compared to their precursor, Cetyl Ricinoleate (Code CR); and C. Benzoate esters of octyl hydroxystearate (Code BOHS) are compared to their precursor, octyl hydroxystearate (Code OHS; Octyl=2-ethylhexyl).

to equalize or come close to the specific gravity of water, which is a measuring gradient for emulsion stability and ease of emulsification. The viscosity of the benzoate esters of the invention are not radically changed from their respective precursors, so the benzoate esters of the invention may be substituted for their precursors in formulations.

Absence of odor is an important factor in consumer acceptance of cosmetic and toiletry products. The precursor compounds are found when evaluated to have a typical "fatty" odor, subjectively suggesting "oiliness". In comparison, the benzoate esters of the invention are found to have milder "fatty" odors.

TABLE II

PHYSICAL PROPERTIES OF NOVEL BENZOATE ESTERS COMPARED TO RESPECTIVE PRECURSORS

| | Group A | | Group B | | Group C | |
|---|---|---|---|---|---|---|
| | Ester Code BCO | Precursor Code CO | Ester Code BCR | Precursor Code CR | Ester Code BOHS | Precursor Code OHS |
| Properties: | | | | | | |
| APPEARANCE: | clear liquid | clear liquid | clear liquid | clear liquid | clear liquid | clear liquid |
| COLOR | light yellow/amber | yellow to light amber | light yellow to amber | light yellow | light amber | light yellow |
| ODOR | milder than CO | typical fatty CO | mild fatty odor | mild fatty odor | very mild fatty | mild fatty |
| TITER (25° C.) | very slight | very slight | some sediment | some sediment | clear | clear |
| S.G. (25° C.) | 0.982 | 0.949 | 0.915 | 0.874 | 0.928 | 0.883 |
| REFRACTIVE INDEX | 1.4890 to 1.4900 | 1.4785 | 1.4720 to 1.4780 | 1.4580 | 1.4740 to 1.4760 | 1.4575 |
| VISCOSITY* (cps.) | 937 | 770 | 80 | 65 | 110 | 80 |
| TASTE | same as CO | typical fatty | bland mild | bland mild | bland mild | bland mild |

*Brookfield Viscometer, Spindle # 1, 10 rpm.

The benzoate esters of the invention are superior to their respective precursor single esters/triglycerides in refractive index and specific gravity. Increased specific gravity is better Solubility Characteristics The solubility characteristics of the novel benzoate esters of the invention are tabulated in Table III. These novel benozate esters are soluble in most commonly used solvents, emollients and vehicles employed in cosmetic product formulations. The novel benzoate esters of the invention are advantageously versatile due to their solubility/compatibility with commonly used emollients, esters, mineral oils, etc.

Solubility/Solvency Tables IVA and IVB show the solubility and concentrations of the sunscreen ingredient in the novel esters of the invention compared to their precursor raw materials (non-benzoate esters). In all cases the novel benzoate esters of the invention allow higher concentrations of the respective sunscreen ingredient. The novel benzoate-

TABLE III

SOLUBILITY/COMPATIBILITY OF NEW BENZOATE ESTERS

| | Group A | | Group B | | Group C | |
|---|---|---|---|---|---|---|
| | Ester Code BCO | Precursor Code CO | Ester Code BCR | Precursor Code CR | Ester Code BOHS | Precursor Code OHS |
| Solvents: | | | | | | |
| Water | -- | -- | -- | -- | -- | -- |
| Propyleneglycol | -- | -- | Disp | -- | Disp | -- |
| Ethanol | -- | + | Disp | + | Disp | + |
| Mineral Oil | Disp | + | + | + | + | + |
| Glycerine | -- | Disp | -- | -- | -- | -- |
| DOW CORNING ® Fluid 244 | -- | Disp | + | + | + | + |
| Finsolv ® BOD | + | + | + | + | + | + |
| Finsolv ® EMG 20 | + | -- | + | -- | + | -- |
| Finsolv ® EB | + | + | + | + | + | + |
| Finsolv ® P | + | + | + | + | + | + |
| Finsolv ® PL62 | + | + | + | + | + | + |
| Finsolv ® PL355 | + | + | + | + | + | + |
| Finsolv ® PG22 | + | + | + | + | + | + |
| Finsolv ® SB | + | + | + | + | + | + |
| Finsolv ® TN | + | + | + | + | + | + |
| Finester EH25 | + | + | + | + | + | + |

Key: Disp indicates dispersible; + indicates soluble; -- indicates insoluble.
TRADE NAME      CTFA NAME*
Finsolv ®   BOD:     Octyldodecyl benzoate
Finsolv ®   EMG20:   Methyl Gluceth 20-benzoate (an ethoxylated methyl glucoside)
Finsolv ®   EB:      2-ethylhexyl benzoate
Finsolv ®   P:       PPG-15 stearyl ether benzoate
Finsolv ®   PL62:    Poloxamer 182 Dibenzoate
Finsolv ®   PL355:   Poloxamer 105 Benzoate
Finsolv ®   PG22:    Dipropylene Glycol Dibenzoate
Finsolv ®   SB:      Isostearyl Benzoate
Finsolv ®   TN:      C12–C15 Alkyl Benzoate
Finester    EH25:    C12–C15 Alcohols Octanoate
Finsolv ® is a registered trademark and Finester is a
trademark of Finetex, Inc., Elmwood Park, New Jersey, 07407.
*Identification is in accordance with the CTFA Cosmetic Ingredient
Dictionary, 5th Ed., 1993. (Published by The Cosmetic, Toiletry, and
Fragance Association, Inc.

Sunscreen Solubility in Novel Benzoate Esters

The two most commonly used solid organic crystalline sunscreens are Benzophenone-3 (2-hydroxy-4-methoxy benzophenone) and PARSOL® 1789 (butyl-methoxy dibenzoyl methane). These two sunscreens are difficult to dissolve and keep in solution for use in sunscreen formulations for optimal SPF (sun-protection factors). Higher solvency for a sunscreen ingredient is desirable as it allows higher concentrations of the sunscreen active ingredient in a formulation. This advantageously raises the SPF ratings for the formulation. The liquid organic sunscreens that are commonly used are octyl-methoxy cinnamate (OMC) and octyl salicylate (OS).

esters of this invention exhibit superiority over their precursor materials and also some commonly used and marketed cosmetic emollients/materials.

The high solvency exhibited by the novel benzoate esters of the invention for the solid crystalline organic sunscreens is an advantageous effect in formulating sunscreen products for the skin-care and hair-care markets. Thus, besides being cosmetic emollients, these novel esters are excellent solvents for the above mentioned sunscreens.

A further aspect of this invention is that these esters, besides being solubilisers for the sunscreens, render anti-washoff effects. This effect is very attractive in formulating long lasting sunscreen products allowing the sunscreen to remain on the skin for a longer duration.

TABLE IV A

SUNSCREEN SOLUBILITIES IN NOVEL BENZOATE ESTERS COMPARED TO RESPECTIVE PRECURSORS

| | | A | | B | | C | |
|---|---|---|---|---|---|---|---|
| Sunscreen Concentrations**: | | Ester Code BCO | Precursor Code CO | Ester Code BCR | Precursor Code CR | Ester Code BOHS | Precursor Code OHS |
| | | | | Sunscreen: BENZOPHENONE-3* | | | |
| 30° C. | 10 | + | + | + | + | + | + |
| 30° C. | 15 | + | + | + | + | + | + |
| 23° C. | 10 | + | + | + | + | + | + |
| 23° C. | 15 | + | -- | + | -- | + | -- |

+ = Soluble, no crystallization
-- = Insoluble, with crystallization
*Benzophenone 3 = 2 hydroxy-4-methoxy-benzophenone
**Concentrations: gms of sunscreen in total of 100 gms of the mixture (total made with Ester/Precursor)

TABLE IV B

SUNSCREEN SOLUBILITIES IN NOVEL BENZOATE ESTERS COMPARED TO RESPECTIVE PRECURSORS

| | | A | | B | | C | |
|---|---|---|---|---|---|---|---|
| Sunscreen Concentrations**: | | Ester Code BCO | Precursor Code CO | Ester Code BCR | Precursor Code CR | Ester Code BOHS | Precursor Code OHS |
| | | | | Sunscreen: PARSOL ®* | | | |
| 30° C. | 5 | + | + | | | | |
| 30° C. | 10 | + | -- | + | + | + | + |
| 30° C. | 15 | + | -- | + | + | + | + |
| 23° C. | 10 | + | -- | + | + | + | + |
| 23° C. | 15 | -- | -- | + | -- | + | -- |

+ = Soluble, no crystallization
-- = Insoluble, with crystallization
*Parsol ® 1789 = butyl-methoxy dibenzoyl methan. PARSOL is a registered trademark of Givaudan Corp. of Clifton, N.J.
**Concentrations: gms of sunscreen in total of 100 gms of the mixture (total made with Ester/Precursor)

Refractive Index

This property is important in formulating clear liquid or solid products for skin care. The refractive indices are tabulated in Table V below. In the case of the novel benzoate esters of the invention, the refractive index is greater than the corresponding precursor oil or ester.

TABLE V

REFRACTIVE INDEX OF NOVEL BENZOATE ESTERS COMPARED TO RESPECTIVE PRECURSORS

| Group | A | | B | | C | |
|---|---|---|---|---|---|---|
| Ester Code | BCO | | BCR | | BOHS | |
| Precursor Code | | CO | | CR | | OHS |
| | Range | Typical | Range | Typical | Range | Typical |
| Refractive Index at 25° C. | 1.4890 to 1.4900 | 1.4785 | 1.4770 to 1.4780 | 1.4580 | 1.4740 to 1.4760 | 1.4575 |

Dispersing Efficacy/Dispersants for organic pigments (white and colors)

The cosmetics industry uses quite a number of organic pigments that are insoluble in oils and are ground for fine particle size before mixing into the formulation system. The finer the particle size, the better the dispersion and color value, as well as the better the spreading effect for better coverage on the skin surface. Commonly used pigments are Titanium Dioxide (TiO2), Red No. 6 Barium Lake and Red No. 21 (a water soluble pigment for dyeing rather than simply coloring).

The novel benzoate esters of the invention were tested for pigment and dye dispersing efficacy. Color pastes were prepared by dispersing dry pigment into the oil phase while hand stirring and then passing each mixture through a three roll mill six times, collecting a 16 oz. sample after each pass. The samples collected were subjected to particle size measurements. Table VI-A shows the results of particle size reduction for the benzoate esters of the invention as compared to their precursors. Specifically, benzoate of castor oil (BCO) was compared to its precursor castor oil; benzoate of cetyl ricinoleate (BCR) was compared to its precursor cetyl ricinoleate (CR); and benzoate of octyl hydroxy stearate (BOHS) was compared to castor oil (CO), a leading ingredient most commonly used in such applications.

The data in Table VI-A shows that in the case of $TiO_2$ dispersions, the BCR ester continued giving better reduction of particle size on the third pass and onwards, as compared to its precursor CR. In the case of the BCR ester, particle size was reduced to one-third the starting size reflecting its very good grinding efficiency. The BCO ester and BOHS ester both followed similar trends in further reducing particle size. A similar trend is shown in grinding efficiency on Red No. 21.

Viscosity of Pigment Dispersions/High Loading of Pigments

Table VI-B shows the viscosities of $TiO_2$ and Red No. 21 dispersions as measured on a Brookfield Viscometer LVT-D at 12 rpm. All three groups of benzoate esters of this invention, i.e., BCO, BCR and BOHS, give a much lower viscosity of $TiO_2$ dispersions which allows for pigment dispersions of higher loadings. The dispersions of Red No. 21 also indicate that the BCR ester shows excellent low viscosity dispersion permitting higher loadings of pigments at lower viscosity.

TABLE VI A

HAGMAN READINGS

| Pass No. | CO | CR | BCR | BCO | BOHS |
|---|---|---|---|---|---|
| | TITANIUM DIOXIDE (50%) | | | | |
| 1 | ≦24 µm | ≦93 µm | ≦30 µm | ≦30 µm | ≦20 µm |
| 2 | ≦14 µm | ≦80 µm | ≦30 µm | ≦26 µm | ≦14 µm |
| 3 | ≦14 µm | ≦80 µm | ≦21 µm | ≦20 µm | ≦14 µm |
| 4 | ≦14 µm | ≦76 µm | ≦18 µm | ≦10 µm | ≦10 µm |
| 5 | ≦12 µm | ≦50 µm | ≦10 µm | ≦10 µm | ≦9 µm |
| 6 | ≦11 µm | ≦43 µm | ≦10 µm | ≦8 µm | ≦8 µm |
| | RED NO. 6 BARIUM LAKE (35%) | | | | |
| 1 | ≦28 µm | ≦49 µm | ≦53 µm | ≦49 µm | N/A |
| 2 | ≦20 µm | ≦48 µm | ≦50 µm | ≦45 µm | N/A |
| 3 | ≦16 µm | ≦40 µm | ≦46 µm | ≦42 µm | N/A |
| 4 | ≦12 µm | ≦38 µm | ≦33 µm | ≦40 µm | N/A |
| 5 | ≦10 µm | ≦33 µm | ≦30 µm | ≦36 µm | N/A |
| 6 | ≦9 µm | ≦30 µm | ≦27 µm | ≦33 µm | N/A |
| | RED NO. 21 (35%) | | | | |
| 1 | ≦40 µm | ≦39 µm | ≦34 µm | ≦39 µm | N/A |
| 2 | ≦29 µm | ≦36 µm | ≦26 µm | ≦30 µm | N/A |
| 3 | ≦20 µm | ≦30 µm | ≦20 µm | ≦26 µm | N/A |
| 4 | ≦12 µm | ≦26 µm | ≦12 µm | ≦14 µm | N/A |
| 5 | ≦10 µm | ≦18 µm | ≦8 µm | ≦12 µm | N/A |
| 6 | ≦10 µm | ≦14 µm | ≦6 µm | ≦10 µm | N/A |

TABLE VI B

VISCOSITY READINGS
Brookfield LVT-D @ 12 RPM

| Pass No. | CO | CR | BCR | BCO | BOHS |
|---|---|---|---|---|---|
| | TITANIUM DIOXIDE (50%) | | | | |
| 1 | 11,934 cps | Out of instrument range | 1794 cps | 6552 cps | 1170 cps |
| 2 | 10,998 cps | Out of instrument range | 1872 cps | 7176 cps | 1170 cps |
| 3 | 11,232 cps | Out of instrument range | 2028 cps | 7800 cps | 1326 cps |
| 4 | 11,154 cps | Out of instrument range | 2028 cps | 7332 cps | 1326 cps |
| 5 | 11,232 cps | Out of instrument range | 2028 cps | 7176 cps | 1326 cps |
| 6 | 11,076 cps | Out of instrument range | 1950 cps | 6786 cps | 1326 cps |
| | RED NO. 21 (35%) | | | | |
| 1 | 12,090 cps | Out of instrument range | 4602 cps | >15,600 cps | N/A |
| 2 | 13,494 cps | Out of instrument range | 4368 cps | >15,600 cps | N/A |
| 3 | 13,026 cps | Out of instrument range | 4212 cps | >15,600 cps | N/A |
| 4 | 12,948 cps | Out of instrument range | 4134 cps | >15,600 cps | N/A |
| 5 | 13,260 cps | Out of instrument range | 4290 cps | >15,600 cps | N/A |
| 6 | 13,728 cps | Out of instrument range | 4368 cps | >15,600 cps | N/A |

Use in Cosmetics Formulations

The tactile characteristics of the novel benzoate esters of the invention were determined by applying the appropriate material, neat or as a dilution with another emollient ester, lanolin or petroleum. The properties were evaluated organoleptically after application to the interior surface of the forearm. The tests conducted were subjective in nature—individuals were requested to evaluate the tactile characteristics no using a scale of 1 to equal "worst" to 5 for "best". The results are set forth in Table VII below, from which it will be seen that the organoleptic properties of the novel benzoate esters of the invention are significantly better than the precursor castor oil. In particular, the benzoate ester compositions of the invention display an unusual lack of greasiness. When combined with "greasy, tacky" materials such as lanolin or petrolatum, the novel esters countered and overcame the negative effects/characteristics. Such properties are very significant in typical applications in which ester products of the present invention are used.

TABLE VII

COSMETIC APPLICATIONS OF NOVEL BENZOATE ESTERS
COMPARED TO CASTOR OIL

| PRODUCT CODE EXAMPLE NOS. | CO Control | BCO 1–5 | BHCO 6, 7 | BCR 8–11 | BOHS 12–15 |
|---|---|---|---|---|---|
| PROPERTIES/EFFECTS: | | | | | |
| SPREADABILITY | 2 | 4 | 3 | 3 | 4 |
| OVERALL TACTILITY | 1 | 3 | 3 | 4 | 3 |
| TACK | 1 | 2 | 3 | 3 | 3 |
| GREASINESS/ OILINESS | 1 | 4 | 4 | 4 | 4 |

Ratings: 1 = Worst 5 = Best
Product Codes:
CO = Castor Oil
BCO = Benzoates of Castor Oil
BHCO = Benzoate of Hydrogenated Castor Oil
BCR = Benzoate of Cetyl Ricinoleate
BOHS = Benzoate of Octyl-Hydroxy Stearate Toxicity Ocular and dermal irritation toxicological studies were performed on BCO, BCR and BOHS using Epiocular Corneal Model and Epiderm Skin Model In-Vitro Toxicity Testing System by MatTek Corporation. Epiocular protocols were run using the test products as is (neat 100%) and 10% in corn oil along with parallel tests on FINSOLV® TN as a reference article. FINSOLV® TN is a $C_{12}$–$C_{15}$ alkyl benzoate and is a very commonly used ingredient in diverse areas of cosmetics, skin and hair care products. Epiderm protocols were run using the test product at 10% and 1% in corn oil with parallel tests on FINSOLV® TN as a reference article.

Under the conditions of the epiocular tests, the test articles had ocular irritation potentials similar to that of the reference article. As the ET-50 (estimated time to cause 50% inhibition) for all articles, at 100%, is greater than 60 minutes, their expected in-vivo irritancies would be very mild to innocuous.

Under the conditions of the epiderm test, the test articles had dermal irritation potentials similar to that of the reference article. As the ET-50 (estimated time to cause 50% inhibition) for both articles, at 10%, is greater than 24 hours, they would be expected to be classified as non-irritating when tested in-vivo. The other novel esters of the invention should have similar toxicological profiles.

Thus, the benzoate ester products of this invention are completely distinctive from and superior to their precursor single esters/triglycerides in all important characteristics for the uses of the products in cosmetic and toiletry formulations.

It is understood that the embodiments described herein are merely exemplary and that a person skilled in the art may make many variations and modifications without departing from the spirit and scope of the invention. All such modifications and variation are intended to be included within the scope of the invention described herein.

What is claimed is:

1. A composition of matter comprising the benzoic acid ester of glyceral tri-ricinoleate.
2. A composition of matter comprising the benzoic acid ester of hydrogenated castor oil.
3. A composition of matter comprising the benzoic acid ester of cetyl ricinoleate.
4. A composition of matter comprising the benzoic acid ester of octyl hydroxy stearate.
5. A composition of matter comprising the benzoic acid ester of hydroxy stearic acid.

* * * * *

UNITED STATES PATENT AND TRADEMARK OFFICE
CERTIFICATE OF CORRECTION

PATENT NO. : 5,959,130
DATED : Sep. 28, 1999
INVENTOR(S) : Ismail Walele and Samad A. Syed It is certified that error appears in the above-indentified patent and that said Letters Patent is hereby corrected as shown below:

Column 1, line 44, delete "inannitol" and insert therefor --mannitol--.

Column 5, line 20, delete "behzoate" and insert therefor --benzoate--.

Column 14, line 33, delete "BCR3 and insert therefor --BCR$^3$--.

Column 24, line 9, delete "glyceral" and insert therefor --glycerol--.

Signed and Sealed this

Eighteenth Day of April, 2000

Attest:

Q. TODD DICKINSON

*Attesting Officer*   *Director of Patents and Trademarks*